United States Patent [19]

Berman et al.

[11] Patent Number: 4,987,073

[45] Date of Patent: Jan. 22, 1991

[54] BACTERIOPHAGE CLONING SYSTEM FOR THE CONSTRUCTION OF DIRECTIONAL DNA LIBRARIES

[75] Inventors: Michael L. Berman, Potomac; P. Scott Meissner, Barnesville; William P. Sisk, Kensington, all of Md.

[73] Assignee: Akzo N.V., Arnhem, Netherlands

[21] Appl. No.: 494,844

[22] Filed: Mar. 14, 1990

Related U.S. Application Data

[63] Continuation-in-part of Ser. No. 366,270, Jun. 12, 1989, abandoned, which is a continuation of Ser. No. 45,099, May 1, 1987, abandoned.

[51] Int. Cl.$^5$ .................. C12P 19/34; C12N 15/00; C07H 15/12
[52] U.S. Cl. .................. 435/172.3; 435/91; 435/320.1; 536/27; 935/8; 935/18; 935/77; 935/80
[58] Field of Search .............. 536/27; 435/172.3, 320, 435/91, 235; 935/18, 31, 32, 26, 77, 80, 8

[56] References Cited

U.S. PATENT DOCUMENTS 4,666,839  5/1987  Souza ................................ 435/91

OTHER PUBLICATIONS

Messing et al., Gene, 19:269-276 (1982).
Molecular Biologicals–Pharmacia Catalog, 1984.
Rougeon, F. and Mach, B. (1976), *Proc. Natl. Acad. Sci. USA*, 73:3418-3422.
Efstratiadis, A., Kafatos, F. C., Maxam, A. M. and Maniatis, T. (1976), *Cell*, 7:279-287.
Okayama, H. and Berg, P. (1982), *Molecular and Cellular Biology*, 2, 161-170.
Alexander, D. C., McKnight, T. D. and Williams, B. G. (1984), *Gene*, 31:79-89.
Helfman, D. M., Feramisco, J. R., Fiddes, J. C., Thomas, G. P. and Hughes, S. H. (1983), *Proc. Natl. Acad. Sci. U.S.A.*, 80:31-35.
Huynn, T. V., Young, R. A. and Davis, R. W. (1984), In: DNA Cloning Techniques: A Practical Approach (Glover, D., ed), "Constructing and Screening cDNA Libraries in Lambda-gt10 and Lambda-gt11", IRL Press, Oxford.
Young, R. A. and Davis, R. W. (1983), *Proc. Natl. Acad. Sci. U.S.A.*, 80:1194-1198.
Kraus, J. P., Williamson, C. L., Firgaira, F. A., Yang-Feng, T. L., Munke, M., Francke, U. and Rosen, L. E. (1986), *Proc. Natl. Acad. Sci. U.S.A.*, 83:2047-2051.
Gubler, U. and Hoffman, B. J. (1983), *Gene*, 25:253-269.
Ransom, J. H., Evans, C. H., McCabe, R. P., Pomato, N., Heinbaugh, J. A., Chin, M., and Hanna, M. G., Jr. (1985), *Cancer Research*, 45:851-862.
Zagrusky, R. J., Baumeister, K., Lomax, N., Berman, M. L. (1985), *Gene Anal. Tech.* 2:89-94.
Sanger, F., Nicklen, S., Coulson, A. R. (1977) *Proc. Natl. Acad. Sci. U.S.A.*, 74, 5463-5467.
Vieria, J. and Messing, J. (1982), *Gene*, 19:259-268.
McCleland, M. and Nelson, M. (1986) *Nuc. Ac. Res.*, 13:r201-r238.
Raleigh, E. A. and Wilson, J. (1986), *Proc. Natl. Acad. Sci. U.S.A.*, 83, 9070-9074.
Gray, P. W., Leung, D. W., Pennica, D., Yelverton, E., Najarian, R., Simonsen, C. C., Derynck, R., Sherwood, P. J., Wallace, D. M., Berger, S. L., Levinson, A. D. and Goeddel, D. V. (1982), *Nature*, 295: 503-508.
Celada, R. and Zabin, I. (1979), *Biochemistry*, 18:404-406.

*Primary Examiner*—Robin L. Tieskin
*Attorney, Agent, or Firm*—Donna Bobrowicz; William M. Blackstone

[57] ABSTRACT

A bacteriophage directional cloning vector containing a multiple cloning site, a method for preparing cDNAs that can be cloned in a unique orientation and a bifunctional oligodeoxynucleotide linker, which creates a unique restriction site when ligated to the 3' end of cDNA fragments. The simple and efficient cDNA cloning system reduces the amount of RNA and effort required for the preparation of large directionally cloned libraries by providing a unique vector that accepts cDNA fragments in a unique 5'-3' orientation and by providing a unique bifunctional linker that facilitates the preparation of cDNA fragments that can be ligated directionally into the vector.

10 Claims, 3 Drawing Sheets

FIG. 2(A)   $^P$NNN———//———AAAAA$_{OH}$
            $_{HO}$NNN———//———TTTTT$_P$

FIG. 2(B)   $^P$GCTTGGATCCAAGC$_{OH}$
            $_{HO}$CGAACCTAGGTTCG$_P$
                    BamHI

FIG. 2(C)

| BamHI | BamHI | BamHI | HindIII BamHI | | BamHI | BamHI | BamHI |
|---|---|---|---|---|---|---|---|
| GCTTGGATCCAAGC | GCTTGGATCCAAGC | GCTTGGATCCAAGC | GCTTGGATCCAAGC | AAAAAA———— | GCTTGGATCCAAGC | GCTTGGATCCAAGC | GCTTGGATCCAAGC NNN |
| CGAACCTAGGTTCG | CGAACCTAGGTTCG | CGAACCTAGGTTCG | CGAACCTAGGTTCG | TTTTTT———— | CGAACCTAGGTTCG | CGAACCTAGGTTCG | CGAACCTAGGTTCG NNN |

FIG. 2(D)
    BamHI                              HindIII'
$^P$GATCCAAGCNNN———//———AAAAA$_{OH}$
$_{HO}$GTTCGNNN———//———TTTTTCGA$_P$

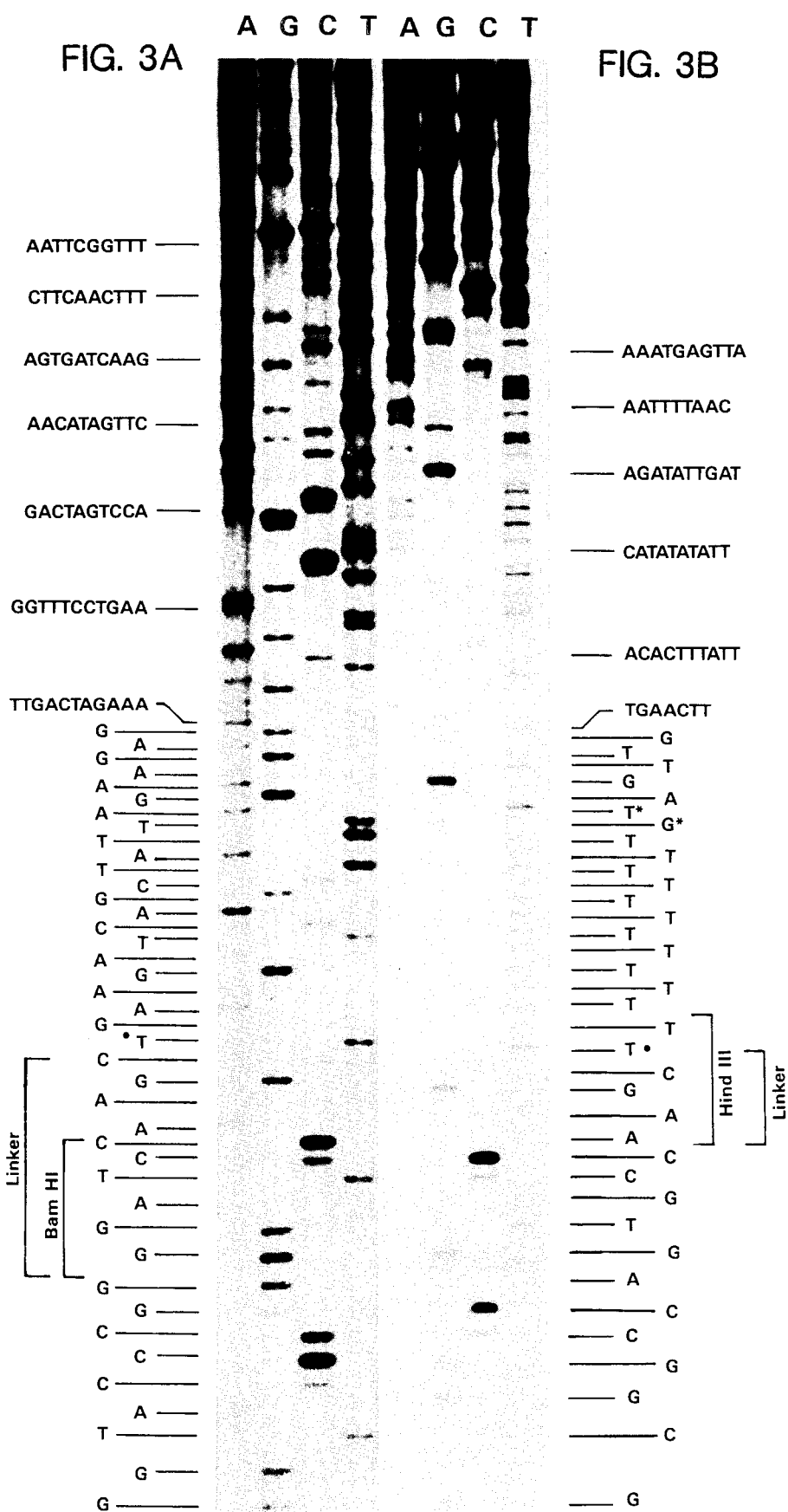

BACTERIOPHAGE CLONING SYSTEM FOR THE CONSTRUCTION OF DIRECTIONAL DNA LIBRARIES

This application is a continuation-in-part of application Ser. No. 07/366,270, filed June 12, 1989, now abandoned, which is a continuation of Application Ser. No. 07/045,099, filed May 1, 1987, now abandoned.

BACKGROUND OF THE INVENTION

Biological research has benefited enormously from the study of genes isolated by cDNA cloning techniques. Since their introduction, (1,2) these techniques have been refined to allow for the isolation of eukaryotic genes expressed at low frequencies. Screening of bacterial libraries using oligonucleotide probes or antibodies to eukaryotic gene products are widely used techniques (3-7). Despite advances, the construction of cDNA libraries still remains an arduous task, particularly if one wishes to construct a directional cDNA library. In directional cloning the vector and fragments to be cloned share an oriented pair of unique endonuclease restriction sites at their termini, which offers efficient cDNA capture and predictable insert orientation. Methods for constructing directional libraries in plasmid vectors exist (3,4,5). However, if phage vectors, particularly bacteriophage vectors, could be used for constructing directional libraries they would greatly simplify the task of constructing and screening large cDNA libraries (6,7). We have developed a new phage vector for the construction of directional libraries that retains many of the useful features of existing bacterial expression vectors.

A directional library constructed in phage would offer several advantages relative to the non-directional libraries constructed with existing phage vectors. The directional library would contain a small number of non-recombinant phage and few, if any, phage would contain cDNA fragments inserted in the incorrect orientation, the directional library would be more efficient in the capture of cDNA fragments due to the high vector:insert ratio, after cleaving the directional vector with endonucleases at the cloning site, subsequent treatment with phosphatase to insure high insertion rates is unnecessary, and DNA inserts in the vector can be cloned in a known orientation relative to vector encoded expression signals.

SUMMARY OF THE INVENTION

We have developed a bacteriophage cloning vector, λORF8, that can be used for the construction of cDNA libraries. The wild-type genome contains five BamHI, five EcoRI, and seven HindIII restriction sites, all of which have been removed from the genome of λORF8. We placed sites for these endonucleases within the multiple cloning site (MCS) of λORF8. We also developed a method for preparing cDNAs that can be cloned in a unique orientation in our phage vector. The method utilizes the synthesis of double-stranded cDNA, including priming of first strand synthesis by oligo-dT. After completion of second strand synthesis, a bifunctional oligodeoxynucleotide linker is ligated to the cDNA fragments. This linker, which contains a BamHI restriction site, creates a HindIII restriction site when ligated to the 3' end of cDNA fragments. Subsequent treatment of methylated cDNA with HindIII and BamHI endonucleases allows these fragments to be cloned directionally into λORF8. The simple and efficient cDNA cloning system of the invention significantly reduces the amount of RNA and effort required for the preparation of large directionally-cloned libraries by providing a unique vector that accepts cDNA fragments in a unique 5'-3' orientation and by providing a unique bifunctional linker that facilitates the preparation of cDNA fragments that can be ligated directionally into the vector.

BRIEF DESCRIPTION OF THE DRAWINGS

FIG. 2 symbolically illustrates the steps in the method for preparing cDNA with unique cohesive termini.

FIG. 3 illustrates the DNA sequence of γ-IFN9 cDNA insert ends.

DETAILED DESCRIPTION OF THE EMBODIMENTS

Figures 1A, 1B, 1C:
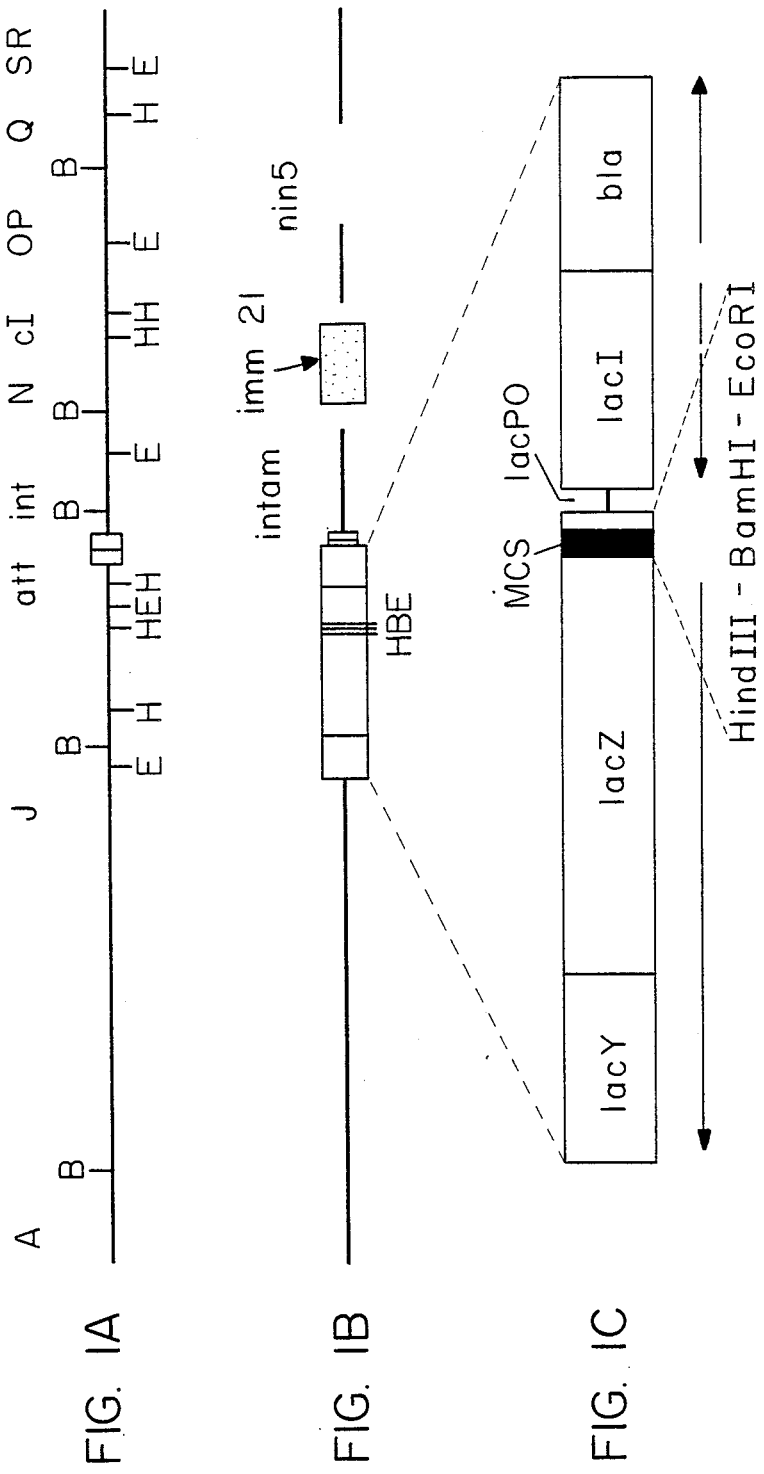
FIG. 1 is a diagram of bacteriophage cloning vector λORF8.

Bacteriophage cloning vectors have properties that make them excellent tools for the construction of cDNA libraries (6). However, in the existing phage vectors that have been available until now cDNA fragments are inserted randomly. Moreover, the background level of non-recombinant phage in such libraries are high in proportion to total phage (7). These limitations substantially increase the number of phage that must be analyzed to detect a gene of interest, and they are a particular problem in vectors designed for expression of cDNA inserts in $E.$ $coli$. These problems are avoided with our novel vector, λORF8, because it accepts cDNA fragments in a unique 5'-3' orientation. In addition, our novel bifunctional linker facilitates the preparation of cDNA fragments that can be ligated directionally into the vector. Taken together, these developments dramatically increase the ease and efficiency of constructing large directional cDNA libraries.

The cloning vector of this invention, λORF8, possesses a multiple cloning site (MCS) containing unique recognition sequences for the restriction enzymes BamHI, EcoRI and HindIII. A method for preparing cDNA fragments with appropriate cohesive termini is needed to use this vector for directional cloning. The methods available before the present invention were either not applicable to phage (3), or involved steps, such as treatment with S1 nuclease, that tended to produce truncated cDNAs (5,8). In order to overcome the limitations of the then available methods, we developed a procedure for preparing cDNA fragments that could be cloned directionally into our phage vector. The procedure is as follows: (i) double stranded cDNA (ds cDNA) is prepared using oligo-dT as the primer for first strand synthesis (9), (ii) ds cDNA is treated with specific methylases to protect internal BamHI and HindIII sites, (iii) the cDNA insert is ligated to a bifunctional oligodeoxynucleotide linker that contains a BamHI site and will form an additional HindIII site when ligated to the 3' end of ds cDNA, (iv) linkers are then digested with HindIII and BamHI and the cDNA insert is ligated into λORF8, cleaved with HindIII and BamHI.

To demonstrate the utility of this cloning system, we prepared a phage library from 5 μg of mRNA isolated from phytohemagglutinin (PHA)-stimulated human peripheral blood lymphocytes (PBLs). The primary library contained $2 \times 10^8$ plaque forming phage, at least 80 percent of which contained inserts. Phage from the library were analyzed for the presence of cDNA inserts and for the presence of the expected BamHI and HindIII sites created by the bifunctional linker. In addition, to verify that our system was capable of efficiently capturing cDNAs, we screened a portion of the library for the presence of gamma interferon (γIFN), a gene expressed at low levels in PHA stimulated peripheral blood lymphocytes.

Our novel bacteriophage cloning vector, λORF8, is useful for the construction of cDNA expression libraries. A diagram of λORF8 is shown in FIG. 1. Cloning in the vector can be achieved with DNA fragments containing EcoRI-BamHI, EcoRI-HindIII or BamHI-HindIII cohesive termini.

The multiple cloning site of λORF8 used for insertion of foreign DNA is located within the lacZ gene. Due to the synthesis of β-galactosidase from lacZ, λORF8 produces blue plaques on a (lacZ) host in the presence of the chromogenic indicator 5-bromo-4-chloro-3-indolyl β-D-galactoside (X-gal). When cDNA fragments are inserted into the multiple cloning site to produce a recombinant phage colorless plaques are the result of insertion, which can easily be distinguished from the blue plaques produced by non-recombinants expressing β-galactosidase. The results of vector DNA ligated in the absence or presence of cDNA are presented in Table 1.

Phage vector designs that include cloning sites within functional genes, e.g., lacZ, provide convenient phenotypes for determining the efficiency of the system (6,7). For example, the lacZ insertion vector λgt11 uses a naturally occurring EcoRI site at codon 1006 of lacZ. Insertions or deletions that alter this region of lacZ invariably result in the synthesis of inactive β-galactosidase monomers.

In vector λORF8 unique cloning sites are located at codons 5-10 of lacZ. Ligation of cDNA fragments into these sites results in the alteration of the lacZ phenotypes of recombinant phage plaques. In contrast to λgt11, there is little specificity for particular amino acid codons in the vicinity of the cloning sites within λORF8. Previous studies of N-terminal β-galactosidase hybrids have shown that the first critical amino acids occur at positions 23-25 in β-galactosidase (20). Therefore, any non-polar insertion in λORF8 that places a ribosome binding site and an initiation codon in frame with lacZ will encode an active β-galactosidase.

Our method for cDNA synthesis requires the protection of internal HindIII and BamHI sites prior to the addition of the DNA linkers. Because HindIII methylase is not commercially available, we used AluI methylase to protect internal HindIII sites. Treatment of HindIII recognition sequences with AluI methylase is known to completely protect these sequences from cleavage by HindIII (17). However, DNA treated with AluI methylase is subject to a restriction system encoded by the mcrB locus of $E.$ $coli$ (18). To prevent possible host restriction of AluI methylated DNA we used $E.$ $coli$ with a mcrB mutation for our primary library.

The use of Alu methylase to protect HindIII sites internal to the cDNA required plating the primary library on a mcrB host. Although we could demonstrate $10^{-3}$ restriction of Alu methylated wild-type lambda (7 HindIII, 143 AluI sites) on a mcrB+ versus mcrB− host, we saw no significant difference in the efficiency of plating on these two hosts of our primary methylated cDNA library. This may be the result of the frequency of AluI sites or the size of the cDNA inserts. However, we have no adequate explanation for this observation. Finally, a number of unrelated cDNA clones that have internal HindIII sites have been isolated from our library, which demonstrates that the Alu methylase is protecting the cDNA as expected.

The design of the cDNA linker takes advantage of the oligo- dT primer at the 3' end of cDNA to create a HindIII site (FIG. 2). Two types of cDNAs will not be cloned by this method. The first type are those cDNAs from which the poly-A tail has been lost during synthesis. The second and more frequent type are cDNAs that have a 5' terminal sequence of pTTNNN. A HindIII site will be formed at both the 5' and 3' ends of these cDNAs when linkers are added. Statistically this class comprises 6.25% of the cDNA products. However, due to the large number of cDNA clones usually obtained using our directional method, these are not serious practical problems.

Another useful feature of λORF8 is the location of the cloning sites within the lacZ gene of the intact lac operon. Consequently, when cDNA encoded open-reading frame segments are inserted in frame with the lacZ sequences, synthesis of eukaryotic peptides are controlled by the lac expression signals. This feature is especially desirable when attempting to isolate genes using antibody probes (7).

An additional benefit of the cloning system described here is its overall simplicity. Beginning with small amounts of mRNA, we have found that a large directional expression library can be constructed easily within 2 days. The cDNA cloning system represents a significant increase in the ease and efficiency with which large directional libraries can be prepared.

Illustrated in FIG. 2, we developed a method that generates cDNA that can be cloned in a unique orientation into the BamHI-HindIII sites of λORF8. A library was constructed from 5 μg of mRNA isolated from PHA-stimulated PBLs. To examine the library for the presence of cDNA inserts, 10 colorless plaques were chosen at random. The phage DNA was co-digested with BamHI and HindIII and the enzyme reactions were resolved on a 1% agarose gel. The analysis revealed that eight of the isolates contained inserts in the size range of 0.5-5Kb, whereas inserts in the remaining two were not detected.

To confirm that the cloning system had generated a library that was truly representative of PHA-stimulated PBLs, we examined $10^5$ plaques for the presence of clones containing γ-IFN sequences. Six clones hybridized to the nick translated probe, and DNA prepared from three of the clones was digested with BamHI and HindIII to examine the size, of the inserts. The expected size of a full length γ-IFN cDNA is about 1.2 Kb (19). One of the clones (λγIFN9) had a BamHI-HindIII insert of 1.2 Kb, while the other two had smaller BamHI-HindIII inserts.

DNA sequence analysis of the 5' vector-cDNA junction of the two smaller clones was obtained by sequencing directly from phage DNA (14). The data showed that these partial cDNA clones initiated within the γIFN gene at nt 493 and 444, respectively. In order to determine the sequence of the 5' and 3' vector-cDNA junctions of the full-length clone, λ-γFN9, the 1.2 Kb BamHI/HindIII insert was subcloned into M13mp18 and M13mp19. Analysis of the sequence showed that the expected linker sequences were present, and the cDNA insert began at nt 2 of the published sequence of γ-IFN (FIG. 3).

FIG. 1. Illustrates a diagram of bacteriophage cloning vector λORF8.

(A) Genetic and physical maps of wild-type phage lambda showing the positions of the naturally occurring BamHI [B] HindIII [H] and EcoRI [E] restriction enzyme sites. Upper case letters above the map refer to the position of some of the phage genes. The positions of the attachment site (att) and the integrase gene (int) are indicated. (B) Genetic and physical map of λORF8. The solid bar refers to wild type sequences, spaces in the line represent deletions of the wild type genome. The open box denotes the cloning region; the black box refers to imm21 control region; the nin5 deletion is shown above the diagram; intam represents an amber mutation at codon 300 of the integrase gene. The size of the vector is 45 Kb (82% wild type lambda) and the cloning capacity is about 9 Kb. (C) Expanded view of cloning region of λORF8. The solid vertical bar refers to the multiple cloning region; lacI, lacZ and lacY are the intact structural genes of the lac operon; bla refers to the β-lactamase gene from pBR322. The arrows below the diagram indicate the directions of transcription. The origin of the MCS is from pUC8/M13mp8 (16) by homologous recombination.

FIG. 2. Illustrates a simplified method for preparing cDNA fragments with unique cohesive termini. (A) Blunt-ended cDNA prepared using oligo-dT as a primer for first strand synthesis. P, represents the 5' phosphate; OH, represents the 3'hydroxyl. (B) Sequence of the 14-mer bifunctional linker; BamHI indicates the internal endonuclease recognition site. (C) Ligation of the linker in [B] to the cDNA results in the formation of concatamers of linkers at the 5' and 3' ends of the cDNA. Note that a single HindIII site is created at the 3' end of the cDNA. (D) Digestion of the cDNA shown in [C] with HindIII and BamHI results in the formation of cDNA fragments containing cohesive termini ('BamHI and HindIII') that can be ligated into BamHI, HindIII cleaved vector.

FIG. 3. Illustrates a DNA sequence of λγFN9 cDNA insert ends. (A) Sequence of the 5' vector/cDNA junction. Vector and BamHI/linker region precede the first cloned γ-IFN nucleotide (●T). This nucleotide corresponds to the nt 2 of the published sequenced (19). The first 93 nt of the cDNA are labeled. (B) Complementary strand sequence of the 3' vector/cDNA junction. Vector, HindIII cloning site/linker region, and the poly-A region adjacent to the terminal nucleotide (●T) of the IFN9 cDNA insert are shown. This clone contains two additional nt (*) not found in the published sequence. The terminal 76 nt of the cDNA clone are labeled.

Table 1. LacZ phenotype of λORF8 plaques from phage arms ligated in the presence and absence of cDNA. Conditions of digestion, ligation and amounts of DNAs are as described in Methods. No LacZ⁻ plaques were observed in the absence of added cDNA. The library screened for γ-IFN is from Experiment 1, which is described in Example 1. Experiment 2, showing results using a different source of cDNA, is provided for comparison.

EXAMPLE 1

Materials. All bacterial strains are $E.\ coli$ K12 derivatives. Bacterial strain MC1061, F⁻ hsdR mcrB araD139 Δ(araABC-leu)7679 galU galK Δ(lac)X74 rpsL thi; or MBM7014.5, F⁻ $^{hsdR}$2 mcrB1 zjj202::Tn10 araD139 araCU25am Δ(argF-lac)U169 trpam malBam supF rpsL relA thi, were used as hosts for the primary cDNA libraries. The hsdR2 and mcrB1 alleles in MBM7014.5 were introduced by P1vir co-transduction with the zjj202::Tn10 insertion from strain ER1351, a generous gift of Elisabeth A. Raleigh (New England Biolabs). Culture conditions and standard media were as described (10). TBA medium was prepared by autoclaving 10 g of tryptone, 5 g of NaCl, and 4 g of agarose in 1 liter of water. DNAse and RNAse were from Sigma, all other enzymes were from New England Biolabs.

RNA Isolation. Ficoll hypaque separated normal human peripheral blood mononuclear leukocytes were incubated at a density of $10^6$ cells/ml in serum-free RPMI 1640 medium containing 5 μg PHA/ml for 24 hours at 37° C. in a $CO_2$ humidified atmosphere (11). Cells were harvested directly into lysis buffer (5M guanidine thiocyanate, 50 mM Tris-HCl pH 7.6, 8% β-mercaptoethanol) and disrupted for 1 minute with a polytron tissue homogenizer, RNA was isolated and messenger RNA was prepared by oligo-dT chromatography as described (12).

Synthesis of cDNA. Beginning with 5 ug mRNA, cDNA was prepared by the method of Gubler and Hoffman (9) using a kit supplied by Amersham. All reactions were carried out in accordance with instructions provided by the manufacturer. The yields from first and second strand synthesis were determined by including 5 μCi 1',2',5' [$^3$H]dCTP (67 Ci/mM) and 50 μCi 5'[α-$^{32}$P]dCTP (3000 Ci/mM) in the first and second strand reactions, respectively. Yields were quantitated by measuring the incorporation of radioactivity into TCA-insoluble material. Based on the percentage of incorporated radioactivity, 500 ng of cDNA were made in the first strand reaction and essentially all of this material was converted to ds cDNA during second strand synthesis. Following treatment with T4 DNA polymerase, the reaction was phenol-chloroform (1:1) extracted and ethanol precipitated. Unincorporated nucleotides were removed by sequential precipitations from 2M ammonium acetate (3). The cDNA was rinsed with 670% ethanol, dried and resuspended in 20 μl of sterile water. The addition of carrier tRNA or glycogen to the cDNA precipitation resulted in inhibition of subsequent ligation reactions. Control reactions carried out in the presence of these carriers showed no such inhibition. Consequently, we did not add exogenous carrier to the cDNA precipitations.

Methylation of cDNA. The cDNA was treated with site specific methylases in order to protect internal restriction enzyme recognition sites from cleavage in subsequent digestions. The cDNA (500 ng) was treated with BamHI and AluI methylases essentially according to directions supplied by the manufacturer (New England Biolabs). The methylation reactions were incubated with 5 units of each enzyme for one hour at 37° C. in buffer (25mM Tris-HCl pH 7.5, 25 mM EDTA, 5 mM β-mercaptoethanol, 80 μM S-adenosylmethionine) in a total volume of 50 ul. The methylated cDNA was phenol-chloroform (1:1) extracted, ethanol precipitated, rinsed, dried and resuspended in 10 μl of water.

Addition of linker. The linker was prepared on a Systec model 1450A automated DNA synthesizer and 100 pmoles (500 ng) were labelled with 50 μCi of 5'[γ-$^{32}$P]-dATP (3000 Ci/mmole) using 10 units of polynucleotide kinase in a 50 μl reaction (50 mM Tris-HCL pH 7.5, 10 mM $MgCl_2$, 1 mM DTT). After 30 minutes at 37° C., unlabelled ATP (final concentration 0.5 mM) and 10 additional units of polynucleotide kinase were added and the reaction was continued for an additional 30 minutes at 37° C. The reaction was terminated by heating for five minutes at 65° C. and the linkers were stored at −20° C. The presence of $^{32}P$ in the oligonucleotide linker made it possible to follow subsequent reactions with the cDNA by polyacrylamide gel electrophoresis and autoradiography (12).

Linkers (50 ng) were ligated to cDNA (500 ng) using 400 units of T4 DNA ligase in 50 mM Tris-HCl, 10 mM MgCl$_2$, 5 mM DTT, 0.2 mM ATP. The ligation was incubated at room temperature for two hours in a volume of 20 μl and was terminated by heating to 65° C. for 10 minutes.

Endonuclease treatment of the linker reaction was accomplished by adding 5 μl of 10× HindIII buffer (0.5M NaCl, 0.5M Tris-HCl pH 8.0, 100 mM MgCl$_2$) and 20 units of HindIII enzyme in a total volume of 50 μl. After 90 minutes at 37° C., 0.5 μl of 5 M NaCl and 20 units of BamHI enzyme were added. Incubation was continued for 60 minutes at 37° C. and the reaction was terminated by heating to 65° C. for 10 minutes.

Unligated linkers and small cDNA fragments were removed by passing the reaction over a Sepharose-CL4B (Pharmacia) column, (prepared in a 1 ml disposable plastic pipette) equilibrated in running buffer (0.3 M NaCl, 10 mM Tris-HCl, pH 7.5, 1 mM EDTA). The 50 μl HindIII and BamHI reaction mixture was adjusted by the addition of 5 μl of 10X running buffer and 5 μl of loading solution (95% glycerol, 0.1% bromophenol blue) before loading on the column. The fractions corresponding to the cDNA fragments were pooled, ethanol precipitated, dried and resuspended in 10 μl water. Analysis of the cDNA fraction by polyacrylamide gel electrophoresis and autoradiography showed that this method eliminated digested linkers and small DNA fragments (12). Preparation of λORF8. Lystates of λORF8 were prepared using standard techniques (10). Phage were banded in cesium chloride and DNA was extracted with formamide (13). Twenty micrograms of phage DNA were treated with 100 units of HindIII for 16 hours at 37° C. in a volume of 100 μl. After phenolchloroform (1:1) extraction and ethanol precipitation, the DNA was digested with 100 units of BamHI for 8 hours at 37° C. in a volume of 100 μl. The buffers used were those recommended by the supplier (New England Biolabs). The DNA was extracted and precipitated as before and resuspended in sterile water at a concentration of 200 μg/ml. Ligation of vector to cDNA. A typical ligation reaction of the cDNA (about 50 ng) to BamHI-HindIII cleaved λORF8 (500 ng) included T4 DNA ligase (400 units) in a total volume of 10 μl of ligation buffer (50 mM Tris-HCl, pH 7.5, 10 mM MgCl$_2$, 5 mM DTT, and 1 mM ATP). After a two hour incubation at room temperature, the ligation reaction was stored at 4° C. overnight, without treatment at 65° C. One microliter of the ligation reaction was removed and packaged according to directions provided by the supplier of the phage packaging extracts (Stratagene Cloning Systems, San Diego, Calif.). As a control to determine the background level of non-recombinants, identical ligation and packaging reactions were performed in the absence of cDNA.

Analysis of the library. To analyze recombinants for the presence of cDNA inserts, high titer lystates (about $10^{10}$ pfu/ml) were prepared from single plaques (10). Lawns of MBM7014 were prepared by combining 0.5 ml of a fresh saturated culture of cells with 5 ml of liquified TBA media. The mixture was poured over a plate containing TBA media, allowed to solidify and about $10^8$ pfu were spread over the plate using 1 ml of 10 mM MgSO$_4$ as diluent. The plate lysates were incubated at 37° C. for about 8 hours, or 30° C. for about 14 hours and then cooled to 4° C. The top-agarose layer was scraped into a 15 ml polypropylene tube (Falcon 2059) containing 50 μl of chloroform, vortexed and then centrifuged at 3,000×g for 15 minutes. The clarified aqueous phase (about 0.5 ml) was removed and transferred to a 1.5 ml microfuge tube and incubated at room temperature for 30 minutes with 5 μl of DNAseI (1 mg/ml in 0.3 M sodium acetate, pH 5) and 5 μl of RNAseA (1 mg/ml in water). Phage DNA was extracted with Tris-saturated phenol (12) followed by two additional phenol-chloroform (1:1) extractions and precipitated from 2M ammonium acetate. A single plate lysate typically yielded several micrograms of DNA. For sequencing directly from DNA (14), the mini-prep DNA was passed over a Sepharose-CL4B column to remove any remaining RNA.

Screening for Gamma interferon recombinants. Approximately $10^5$ recombinants were plated on an mcrB host and transferred on to nitrocellulose filters as described (10). Pre-hybridization, hybridization and nick translation were performed using standard procedures (10, 12). Filters were probed for γ-IFN using a nick translated 1.2 Kb DNA fragment encoding the entire γ-IFN structural gene (a generous gift from R. Dijkema, Organon International BV, Oss, The Netherlands). Following hybridization, filters were washed twice at room temperature for 15 minutes in 2×SSC., 0.1 % SDS (1×SSC is 0.15 M NaCl, 0.015 M sodium citrate), and twice at 55° C. for 15 minutes in 2×SSC., 0.1% SDS. Filters were air dried and exposed for 12 hours at −70° C. on Kodak RP5 X-ray film using a Dupont Cronex intensifying screen.

Subcloning and sequence analysis. Phage clone λ-γIFN9 was digested with BamHI and HindIII, the 1200 bp cDNA insert was gel purified and subsequently ligated into BamHI and HindIII cleaved M13mp18 and M13mp19. Single stranded template DNA was prepared (12) and sequenced by the dideoxy chain terminating method (15). The 5' and 3' insert junctions were determined using the M13mp18 vector and M13mp19 vector respectively. The sequencing reactions were resolved on a 10% polacrylamide 8M urea gel. The sequencing primer (NEB #1200) and sequencing reagents were from New England Biolabs.

TABLE 1

| DNA | Ligase | Experiment | PFU/μg vector DNA Phenotype | |
|---|---|---|---|---|
| | | | Lac$^+$ (%) | Lac$^-$ (%) |
| λ ORF8 | − | 1 | 1 × 10$^3$ (>99) | <1 (1<) |
| | | 2 | 5 × 10$^2$ (>99) | <1 (1<) |
| λ ORF8 | + | 1 | 1 × 10$^7$ (>99) | <1 (1<) |
| | | 2 | 3.3 × 10$^5$ (>99) | <1 (1<) |
| λ ORF8 + cDNA | + | 1 | 8 × 10$^6$ (25) | 3.2 × 10$^7$ (75) |
| | | 2 | 1.5 × 10$^4$ (60) | 1 × 10$^4$ (40) |

1. Rougeon, F. and Mach, B. (1976) *Proc. Natl. Acad. Sci. USA* 73:3418-3422.
2. Efstratiadis, A., Kafatos, F. C., Maxam, A. M. and Maniatis, T. (1976) *Cell* 7:279-287.
3. Okayama, H. and Berg, P. (1982) *Molecular and Cellular Biology* 2 161-170.

4. Alexander, D. C., McKnight, T. D. and Williams, B. G. (1984) *Gene* 31:79–89.
5. Helfman, D. M., Feramisco, J. R., Fiddes, J. C., Thomas, G. P. and Hughes, S. H. (1983) *Proc. Natl. Acad. Sci. USA* 80:31–35.
6. Huynh, T. V., Young, R. A. and David, R. W. (1984) In: DNA Cloning Techniques: A Practical Approach (Glover, D., ed) "Constructing and Screening cDNA Libraries in Lambda-gt10 and Lambda-gt11", IRL Press, Oxford.
7. Young, R. A. and Davis, R. W. (1983) *Proc. Natl. Acad. Sci. USA* 80:1194–1198.
8. Kraus, J. P., Williamson, C. L., Firgaira, F. A., Yang-Feng, T. L., Munke, M., Francke, U. and Rosen, L. E. (1986) *Proc. Natl. Acad. Sci. USA* 83:2047–2051.
9. Gubler, U. and Hoffman, B. J. (1983) *Gene* 25:253–269.
10. Silhavy, T. J., Berman, M. L. and Enquist, L. W. (1984). *Experiments with Gene Fusions*, Cold Spring Harbor Press, Cold Spring Harbor, N.Y.
11. Ransom, J. H., Evans, C. H., McCabe, R. P. Pomato, N., Heinbaugh, J. A., Chin, M., and Hanna, M. G., Jr. (1985) *Cancer Research* 45:851–862.
12. Maniatis, T., Fritsch, E. F., Sambrook, J. (1982) *Molecular Cloning, A Laboratory Manual*, Cold Spring Harbor Press, Cold Spring Harbor, N.Y.
13. Davis, R. W., Botstein, D. and Roth, J. R. (1980) *Advanced Bacterial Genetics, A Manual for Genetic Engineering*, Cold Spring Harbor Press, Cold Spring Harbor, N.Y.
14. Zagrusky, R. J., Baumeister, K., Lomax, N., Berman, M. L. (1985) *Gene Anal. Tech.* 2:89–94.
15. Sanger, F., Nicklen, S., Coulson, A. R. (1977) *Proc. Natl. Acad. Sci. USA* 74, 5463–5467.
16. Vieria, J. and Messing, J. (1982) *Gene* 19: 259–268.
17. McCleland, M. and Nelson, M. (1986) *Nuc. Ac. Res.* 13:r201–r238.
18. Raleigh, E. A. and Wilson, J. (1986) *Proc. Natl. Acad. Sci. USA* 83, 9070–9074.
19. Gray, P. W., Leung, D. W., Pennica, D., Yelverton, E., Najarian, R., Simonsen, C. C., Derynck, R., Sherwood, P. J., Wallace, D. M., Berger, S. L., Levinson, A. D. and Goeddel, D. V. (1982) *Nature* 295: 503–508.
20. Celada, R. and Zabin, I. (1979) *Biochemistry* 18:404–406.

We claim:

1. A highly efficient method for modifying and unidirectionally inserting cDNA into a cloning vector, comprising:
   synthesizing a double stranded oligonucleotide linker comprising a complete restriction enzyme recognition site joined to nucleotides comprising a different and incomplete restriction enzyme recognition site, such sites being in a 5'-incomplete-complete-3' configuration;
   ligating the linker to both ends of a double stranded cDNA fragment to form a cDNA-linker composition such that an incomplete restriction enzyme recognition site is reconstituted to a complete restriction enzyme site only at the 3' poly A end of the cDNA fragment;
   cleaving said cDNA-linker composition with two different restriction enzymes, said enzymes being specific for said restriction sites resulting in a cDNA with two asymmetrical restriction enzyme recognition sites; and
   inserting unidirectionally the cleaved cDNA with asymmetrical restriction enzyme recognition sites into a vector containing complementary asymmetrical sites.

2. A method according to claim 1, wherein said oligonucleotide linker is single stranded.

3. A method according to claim 2, wherein the complete site is a BamHI restriction site bound symmetrically by the nucleotide sequence GCTT.

4. A method according to claim 3, wherein said reconstituted restriction enzyme recognition site is to HindIII endonuclease.

5. A method according to claim 1, wherein said two restriction enzymes are BamHI endonuclease and HindIII endonuclease.

6. A method according to claim 1, wherein said vector is lambda ORF8.

7. A composition consisting essentially of a double stranded cDNA with a ply A end and a double stranded linker which linker contains a complete restriction enzyme recognition site flanked on both ends by a different and incomplete restriction enzyme recognition site which incomplete site contains nucleotides that allow the formation of a complete restriction enzyme recognition site only at the poly A end of the cDNA when the linker and cDNA are incubated under conditions that allow intermolecular ligation.

8. A linker-cDNA composition according to claim 7, wherein said incomplete restriction enzyme recognition site is the partial HindIII restriction site nucleotide sequence of GCTT and said complete restriction enzyme recognition site is the complete BamHI restriction site.

9. A linker-cDNA composition according to claim 7, wherein said reconstituted restriction enzyme recognition site is to HindIII endonuclease.

10. A linker-cDNA composition according to claim 17, wherein said vector is lambda ORF8.

* * * * *